US009115305B2

(12) United States Patent
Cranor et al.

(10) Patent No.: US 9,115,305 B2
(45) Date of Patent: Aug. 25, 2015

(54) BROAD TEMPERATURE PERFORMANCE CHEMILUMINESCENT SYSTEMS AND METHODS

(71) Applicant: Cyalume Technologies, West Springfield, MA (US)

(72) Inventors: Earl Cranor, Longmeadow, MA (US); Linda Jacob, Woodbridge, CT (US); Patrick Taylor, Holyoke, MA (US)

(73) Assignee: Cyalume Technologies, Inc., West Springfield, MA (US)

( * ) Notice: Subject to any disclaimer, the term of this patent is extended or adjusted under 35 U.S.C. 154(b) by 0 days.

(21) Appl. No.: 14/294,050

(22) Filed: Jun. 2, 2014

(65) Prior Publication Data

US 2014/0353559 A1    Dec. 4, 2014

Related U.S. Application Data

(60) Provisional application No. 61/830,075, filed on Jun. 1, 2013, provisional application No. 61/830,071, filed on Jun. 1, 2013, provisional application No. 61/830,072, filed on Jun. 1, 2013, provisional application No. 61/830,070, filed on Jun. 1, 2013.

(51) Int. Cl.
*C09K 11/07* (2006.01)
*C09K 11/02* (2006.01)
*G01N 21/76* (2006.01)

(52) U.S. Cl.
CPC ............. *C09K 11/07* (2013.01); *C09K 11/025* (2013.01); *G01N 21/76* (2013.01); *C09K 2211/1007* (2013.01); *C09K 2211/1018* (2013.01)

(58) Field of Classification Search
USPC .......................................... 252/700; 362/34
See application file for complete search history.

(56) References Cited

U.S. PATENT DOCUMENTS

| | | | |
|---|---|---|---|
| 2012/0097063 A1* | 4/2012 | Cranor et al. ................. | 102/513 |
| 2012/0126188 A1 | 5/2012 | Schrimmer | |
| 2014/0353558 A1 | 12/2014 | Cranor et al. | |
| 2014/0353560 A1 | 12/2014 | Cranor et al. | |
| 2014/0356975 A1 | 12/2014 | Cranor et al. | |

OTHER PUBLICATIONS

International Search Report and Written Opinion from International Application No. PCT/US/2014/040573 dated Oct. 15, 2014.

* cited by examiner

*Primary Examiner* — Vu A Nguyen
(74) *Attorney, Agent, or Firm* — Greenberg Traurig, LLP

(57) ABSTRACT

In some embodiments, the present invention is a chemiluminescent system, including: an oxalate system, including: (a) at least one oxalate ester, (b) at least one first solvent selected from the group consisting of alkyl benzoates, dialkyl phthalates, trialkyl acetylcitrates, 2-acetyloxy isobutyrates, paraffinic liquids, isoparaffinic liquids, toluene, nitroethane, and a combination thereof, (c) at least one second solvent selected from the group consisting of: dialkyl malonates, dialkyl dialkylmalonates, dialkyl arylalkylmalonates, dialkyl succinates, dialkyl glutarates, dialkyl adipates, dialkyl pimelates, dialkyl polyalkylmalonates and a combination thereof, (d) at least one fluorescer, and (e) at least one inorganic salt, and an activator system, including: (a) at least one peroxide, (b) at least one third solvent, (c) at least one fourth solvent, and (d) at least one catalyst.

9 Claims, 1 Drawing Sheet

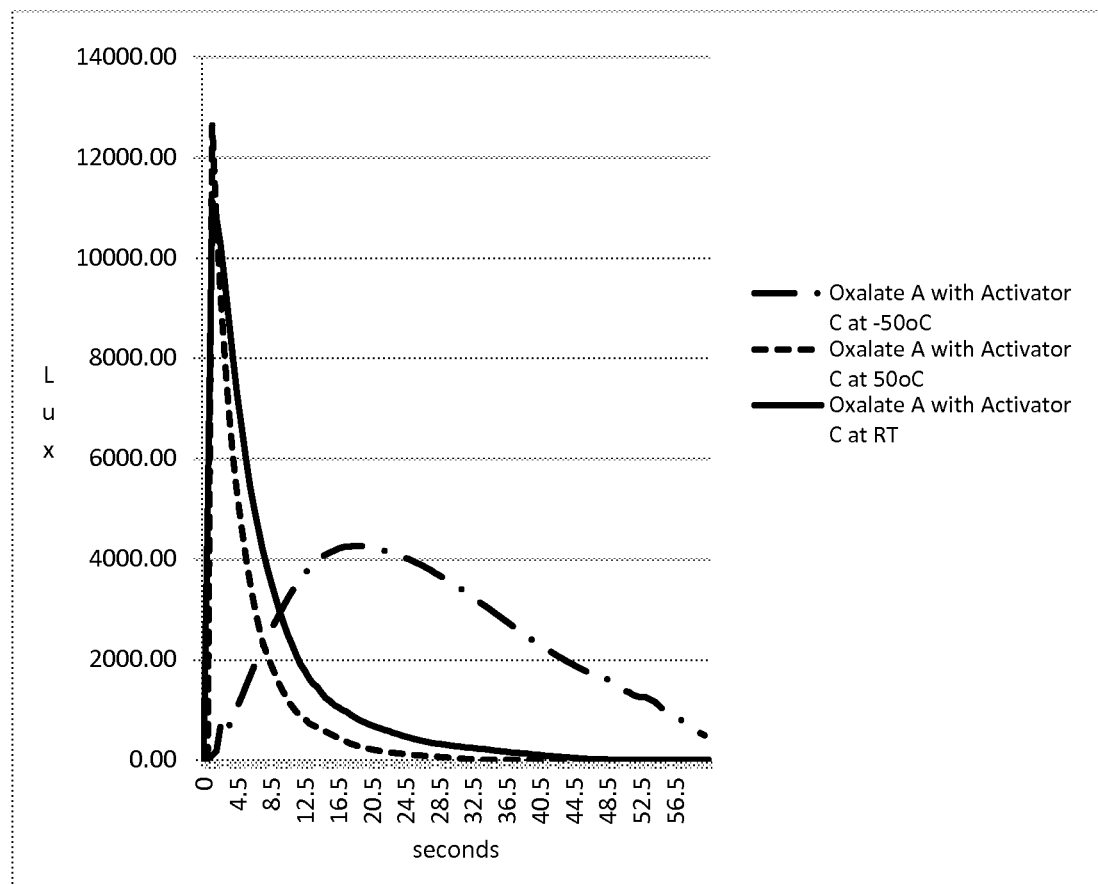

BROAD TEMPERATURE PERFORMANCE CHEMILUMINESCENT SYSTEMS AND METHODS

RELATED APPLICATIONS

This application claims the priority of U.S. provisional applications Ser. No. 61/830,070, filed Jun. 1, 2013, entitled "BROAD TEMPERATURE PERFORMANCE CHEMILUMINESCENT SYSTEMS AND METHODS", Ser. No. 61/830,071, filed Jun. 1, 2013, entitled "LOW TEMPERATURE OXALATE SYSTEMS AND METHODS FOR CHEMILUMINESCENT REACTIONS", Ser. No. 61/830,072, filed Jun. 1, 2013, entitled "LOW TEMPERATURE ACTIVATOR SYSTEMS AND METHODS FOR CHEMILUMINESCENT REACTIONS", and Ser. No. 61/830,075, filed Jun. 1, 2013, entitled "MIXED CATALYST SYSTEMS AND METHODS FOR CHEMILUMINESCENT REACTIONS," which are incorporated herein by reference in their entireties for all purposes.

TECHNICAL FIELD

In some embodiments, the present invention relates to chemiluminescent systems and methods.

BACKGROUND

Chemiluminescence is the emission of light as a result of a chemical reaction. There may also be limited emission of heat during the chemical reaction. Typically, a reaction beginning with reactants A and B, with an excited intermediate, yields products and light. Typically, there are many applications that use chemiluminescence. For example, chemiluminescence is used in gas analysis, analysis of inorganic and/or organic species, detection and assay of biomolecules, DNA sequencing, lighting objects, and children's toys.

BRIEF SUMMARY OF INVENTION

In some embodiments, the present invention is a chemiluminescent system, including: an oxalate system, including: (a) at least one oxalate ester in an amount ranging from 3 to 60 percent by weight based on a total weight of the oxalate system, (b) at least one first solvent selected from the group consisting of: alkyl benzoates, dialkyl phthalates, trialkyl acetylcitrates, 2-acetyloxy isobutyrates, paraffinic liquids, isoparaffinic liquids, toluene, nitroethane, and a combination thereof, where the at least one first solvent is present in an amount ranging from 10 to 97 percent by weight based on the total weight of the oxalate system; (c) at least one second solvent selected from the group consisting of: dialkyl malonates, dialkyl dialkylmalonates, dialkyl arylalkylmalonates, dialkyl succinates, dialkyl glutarates, dialkyl adipates, dialkyl pimelates, dialkyl polyalkylmalonates and a combination thereof, where the at least one second solvent is present in an amount ranging from 5 to 85 percent by weight based on the total weight of the oxalate system; (d) at least one fluorescer, and (e) at least one inorganic salt, in an amount ranging from 0.1 to 30 percent by weight based on the total weight of the oxalate system, and an activator system, including: (a) at least one peroxide, (b) at least one third solvent selected from the group consisting of: tert-butanol, 3-methyl-3-pentanol, 2-methyl-2-butanol, ethyl 2-hydroxyisobutyrate, methyl 2-hydroxyisobutyrate, ethylene glycol, propylene glycol, ethylene glycol monomethyl ether, ethylene glycol diethyl ether, ethylene glycol monobutyl ether, ethylene glycol dibutyl ether, and propylene glycol dimethyl ether, and a combination thereof; where the at least one third solvent is present in an amount ranging from 5 to 85 percent by weight based on the total weight of the activator system, (c) at least one fourth solvent selected from the group consisting of: trialkyl citrates, dialkyl phthalates, glycols, glycol ethers, and a combination thereof; where the at least one fourth solvent is present in an amount ranging from 15 to 95 percent by weight based on a total weight of the activator system, and (d) at least one catalyst, and where the chemiluminescent system, at a temperature ranging from −110 degrees Celsius to 75 degrees Celsius, is configured to produce a light having an illuminescence.

In some embodiments, the at least one oxalate ester is represented by formula (I):

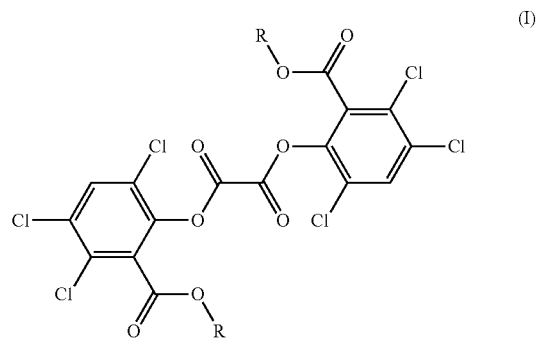

where $R=CH_2A$, and A is selected from the group consisting of an alkyl chain, alkyl ring, an aromatic ring, and a combination thereof, where R is linear or branched, and where R is from $C_{4-15}$.

In some embodiments, the at least one oxalate ester is selected from the group consisting of: bis{3,4,6-trichloro-2-[(2-methylpropoxy)carbonyl]phenyl}oxalate, bis{3,4,6-trichloro-2-[(cyclopropylmethoxy)carbonyl]phenyl}oxalate, bis{3,4,6-trichloro-2-[(2-methylbutoxy)carbonyl]phenyl}oxalate, bis{3,4,6-trichloro-2-[(3-methylbutoxy)carbonyl]phenyl}oxalate, bis{3,4,6-trichloro-2-[(2,2-dimethylpropoxy)carbonyl]phenyl}oxalate, bis{3,4,6-trichloro-2-[(2-methylpentyloxy)carbonyl]phenyl}oxalate, bis{3,4,6-trichloro-2-[(3-methylpentyloxy)carbonyl]phenyl}oxalate, bis{3,4,6-tri chloro-2-[(4-methylpentyloxy)carbonyl]phenyl}oxalate, bis{3,4,6-trichloro-2-[(3,3-dimethylbutoxy)carbonyl]phenyl}oxalate, bis{3,4,6-trichloro-2-[(2-ethylbutoxy)carbonyl]phenyl}oxalate, bis{3,4,6-trichloro-2-[(cyclopentylmethoxy)carbonyl]phenyl}oxalate, bis{3,4,6-trichloro-2-[(2-methylhexyloxy)carbonyl]phenyl}oxalate, bis{3,4,6-trichloro-2-[(3-methylhexyloxy)carbonyl]phenyl}oxalate, bis{3,4,6-trichloro-2-[(4-methylhexyloxy)carbonyl]phenyl}oxalate, bis{3,4,6-trichloro-2-[(5-methylhexyloxy)carbonyl]phenyl}oxalate, bis{3,4,6-trichloro-2-[(cyclohexylmethoxy)carbonyl]phenyl}oxalate, bis{3,46-trichloro-2-[(phenylmethoxy)carbonyl]phenyl}oxalate, bis{3,4,6-trichloro-2-[(2-phenylethoxy)carbonyl]phenyl}oxalate, bis(3,4,6-trichloro-2-{[(2-methylphenyl)methoxy]carbonyl}phenyl)oxalate, bis(3,4,6-trichloro-2-{[(3-methylphenyl)methoxy]carbonyl}phenyl)oxalate, bis(3,4,6-trichloro-2-{[(4-methylphenyl)methoxy]carbonyl}phenyl)oxalate, bis(3,4,6-trichloro-2-{[(2,3-dimethylphenyl)methoxy]carbonyl}phenyl)oxalate, bis(3,4,6-trichloro-2-{[(2,4-dimethylphenyl)methoxy]carbonyl}phenyl)oxalate, bis(3,4,6-trichloro-2-{[3,4- dimethylphenyl)methoxy]carbonyl}phenyl)oxalate, bis(3,4,6-trichloro-2-{[(3,5-dimethylphenyl)methoxy]carbonyl}phenyl)oxalate, bis(3,4,6-trichloro-2-{[(2,6-dimethylphenyl)methoxy]carbonyl}phenyl)oxalate, bis(3,4,6-trichloro-2-{[(2-ethylphenyl)methoxy]carbonyl}phenyl)oxalate, bis(3,4,6-trichloro-2-{[(3-ethylphenyl)methoxy]carbonyl}phenyl)oxalate, bis(3,4,6-trichloro-2-{[(4-ethylphenyl)methoxy]carbonyl}phenyl)oxalate, bis(3,4,6-trichloro-2-{[2-(2-methylphenyl)ethoxy]carbonyl}phenyl)oxalate, bis(3,4,6-trichloro-2-{[2-(3-methylphenyl)ethoxy]carbonyl}phenyl)oxalate, bis(3,4,6-trichloro-2-{[2-(4-methylphenyl)ethoxy]carbonyl}phenyl)oxalate, bis{3,4,6-trichloro-2-[(2-phenylpropoxy)carbonyl]phenyl}oxalate, bis{3,4,6-trichloro-2-[(3-phenylpropoxy)carbonyl]phenyl}oxalate, bis{3,4,6-trichloro-2-[1-naphthalenylmethoxy)carbonyl]phenyl}oxalate, bis{3,4,6-trichloro-2-[2-naphthalenylmethoxy)carbonyl]phenyl}oxalate, bis{3,4,6-trichloro-2-[(2,2-diphenylethoxy)carbonyl]phenyl}oxalate, bis{3,4,6-trichloro-2-[(9-fluorenylmethoxy)carbonyl]phenyl}oxalate, and bis{3,4,6-trichloro-2-[(9-anthracenylmethoxy)carbonyl]phenyl}oxalate.

In some embodiments, the at least one fluorescer is present in an amount ranging from 0.05 to 0.9 percent by weight based on the total weight of the chemiluminescent system.

In some embodiments, the at least one inorganic salt is selected from the group consisting of sodium thiosulphate, potassium thiosulphate, cobalt acetate, copper acetate, lead acetate, cupric chloride, ferric chloride, calcium iodide, potassium iodide, silver nitrate, and a combination thereof.

In some embodiments, the at least one peroxide is selected from the group consisting of hydrogen peroxide, sodium peroxide, sodium perborate, sodium pyrophosphate peroxide, urea peroxide, histidine peroxide, t-butylhydroperoxide, peroxynehzoic acid, sodium percarbonate, and a combination thereof.

In some embodiments, the at least one peroxide is present in an amount ranging from 0.25 to 25 percent by weight based on the total weight of the chemiluminescent system.

In some embodiments, the at least one catalyst is selected from the group consisting of: dimethylbenzylamine, N,N-dimethyl-1-phenylethylamine, N-ethyl-N-methylbenzylamine, diethylbenzylamine, N-methyl-N-propylbenzylamine, N,N-dibutylbenzylamine, N,N-bis(1-methylethyl)benzenemethanamine, methyl dibenzylamine, ethyl dibenzylamine, n-propyl dibenzylamine, iso-propyl dibenzylamine, butyl dibenzylamine, iso-butyl dibenzylamine, N,N-dibenzyl-2-phenylethanamine, hexyl dibenzylamine, tribenzyl amine, 4-methyl-N,N-bis[(4-methylphenyl)methyl]benzenemethanamine, 4-methyl-N,N-bis(phenylmethyl)benzenemethanamine, N-methyl-N-phenylbenzenemethanamine, N-ethyl-N-phenylbenzenemethanamine, N,4-dimethyl-N-phenylbenzenemethanamine, N-propyl-N-phenylbenzenemethanamine, N,N-diphenylbenzenemethanamine, N,N-bis(4-methylphenyl)benzenemethanamine, lithium benzoate, sodium benzoate, potassium benzoate, cesium benzoate, lithium salicylate, sodium salicylate, potassium salicylate, cesium salicylate, lithium o-anisate, sodium o-anisate, potassium o-anisate, cesium o-anisate, lithium p-anisate, sodium p-anisate, potassium p-anisate, and/or cesium p-anisate.

In some embodiments, the at least one catalyst is present in an amount ranging from 5 to 0.0005 percent by weight based on the total weight of the chemiluminescent system.

BRIEF DESCRIPTION OF THE DRAWINGS

The present invention will be further explained with reference to the attached figures. The figures constitute a part of this specification and include illustrative embodiments of the present invention and illustrate various objects and features thereof. The figures shown are not necessarily to scale, with emphasis instead generally being placed upon illustrating the principles of the present invention. Further, some features may be exaggerated to show details of particular components.

FIG. 1 illustrates aspects of some embodiments of the instant invention.

Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DETAILED DESCRIPTION

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

"Activation" and variations thereof, as used herein, means that the oxalate system and the activator system of the present invention have been sufficiently combined such as by mixing to provide useable light in a broad temperature range.

In some embodiments, the present invention relates to chemiluminescent systems. In some embodiments, an exemplary chemiluminescent system of the present invention can be utilized for tracing rounds in munitions that performs at a broad temperature range.

In some embodiments, the present invention is a chemiluminescent system that includes an oxalate system and an activator system, wherein the oxalate system includes at least one oxalate ester, at least one first solvent, at least one dye and at least one inorganic salt, wherein the activator system includes at least one peroxide, at least one second solvent, and at least one catalyst, and wherein the chemiluminescent system is configured so as to provide light in a temperature range from −110 deg C. to 75 deg C.

In some embodiments, the oxalate system includes at least one oxalate ester selected from the group consisting of bis(2, 4,5-trichloro-6-carbopentoxyphenyl)oxalate; bis(2,4,5-trichlorophenyl)oxalate; bis(2,4,5-tribromo-6-carbohexoxyphenyl)oxalate; bis(2,4,5-trichloro-6-carboisopentoxyphenyl)oxalate; bis(2,4,5-trichloro-6-carbobenzoxyphenyl)oxalate; bis(2-nitrophenyl)oxalate; bis(2,4-dinitrophenyl)oxalate; bis(2,6-dichloro-4-nitrophenyl)oxalate; bis(2,4,6-trichlorophenyl)oxalate; bis(3-trifluoromethyl-4-nitrophenyl)oxalate; bis(2-methyl-4,6-dinitrophenyl)oxalate; bis(1,2-dimethyl-4,6-dinitrophenyl)oxalate; bis(2,4-dichlorophenyl)oxalate; bis(2,4-dinitrophenyl)oxalate; bis(2,5-dinitrophenyl)oxalate; bis(2-formyl-4-nitrophenyl)oxalate; bis(pentachlorophenyl)oxalate; bis(1,2-dihydro-2-oxo-1-pyridyl)glyoxal; bis(2,4-dinitro-6-methylphenyl)oxalate; and bis-N-phthalimidyl oxalate.

In some embodiments, the at least one oxalate ester is selected from the group consisting of oxalate esters represented by the general formula (I),

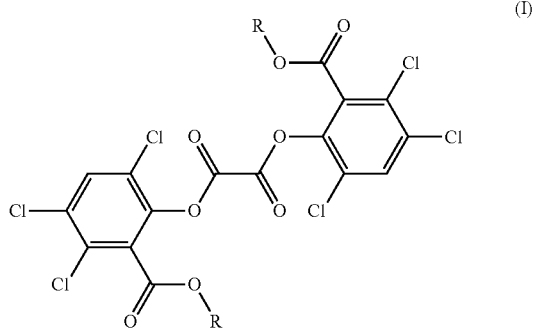

wherein R=CH$_2$A, and A is chosen from alkyl chains, alkyl rings, and aromatic rings or combinations thereof, and wherein R is linear or nonlinear (i.e., branched), and comprises from 4-15 carbon atoms.

In some embodiments, the at least one oxalate ester is selected from the group consisting of bis{3,4,6-trichloro-2-[(2-methylpropoxy)carbonyl]phenyl}oxalate; bis{3,4,6-trichloro-2-[(cyclopropylmethoxy)carbonyl]phenyl}oxalate; bis{3,4,6-trichloro-2-[(2-methylbutoxy)carbonyl]phenyl}oxalate; bis{3,4,6-trichloro-2-[(3-methylbutoxy)carbonyl]phenyl}oxalate; bis{3,4,6-trichloro-2-[(2,2-dimethylpropoxy)carbonyl]phenyl}oxalate; bis{3,4,6-trichloro-2-[(2-methylpentyloxy)carbonyl]phenyl}oxalate; bis{3,4,6-trichloro-2-[(3-methylpentyloxy)carbonyl]phenyl}oxalate; bis{3,4,6-trichloro-2-[(4-methylpentyloxy)carbonyl]phenyl}oxalate; bis{3,4,6-trichloro-2-[(3,3-dimethylbutoxy)carbonyl]phenyl}oxalate; bis{3,4,6-trichloro-2-[(2-ethylbutoxy)carbonyl]phenyl}oxalate; bis{3,4,6-trichloro-2-[(cyclopentylmethoxy)carbonyl]phenyl}oxalate; bis{3,4,6-trichloro-2-[(2-methylhexyloxy)carbonyl]phenyl}oxalate; bis{3,4,6-trichloro-2-[(3-methylhexyloxy)carbonyl]phenyl}oxalate; bis{3,4,6-trichloro-2-[(4-methylhexyloxy)carbonyl]phenyl}oxalate; bis{3,4,6-trichloro-2-[(5-methylhexyloxy)carbonyl]phenyl}oxalate; bis{3,4,6-trichloro-2-[(cyclohexylmethoxy)carbonyl]phenyl}oxalate; bis{3,4,6-trichloro-2-[(phenylmethoxy)carbonyl]phenyl}oxalate; bis{3,4,6-trichloro-2-[(2-phenylethoxy)carbonyl]phenyl}oxalate; bis(3,4,6-trichloro-2-{[(2-methylphenyl)methoxy]carbonyl}phenyl)oxalate; bis(3,4,6-trichloro-2-{[(3-methylphenyl)methoxy]carbonyl}phenyl)oxalate; bis(3,4,6-trichloro-2-{[(4-methylphenyl)methoxy]carbonyl}phenyl)oxalate; bis(3,4,6-trichloro-2-{[(2,3-dimethylphenyl)methoxy]carbonyl}phenyl)oxalate; bis(3,4,6-trichloro-2-{[(2,4-dimethylphenyl)methoxy]carbonyl}phenyl)oxalate; bis(3,4,6-trichloro-2-{[3,4-dimethylphenyl)methoxy]carbonyl}phenyl)oxalate; bis(3,4,6-trichloro-2-{[(3,5-dimethylphenyl)methoxy]carbonyl}phenyl)oxalate; bis(3,4,6-trichloro-2-{[(2,6-dimethylphenyl)methoxy]carbonyl}phenyl)oxalate; bis(3,4,6-trichloro-2-{[(2-ethylphenyl)methoxy]carbonyl}phenyl)oxalate; bis(3,4,6-trichloro-2-{[(3-ethylphenyl)methoxy]carbonyl}phenyl)oxalate; bis(3,4,6-trichloro-2-{[(4-ethylphenyl)methoxy]carbonyl}phenyl)oxalate; bis(3,4,6-trichloro-2-{[2-(2-methylphenyl)ethoxy]carbonyl}phenyl)oxalate; bis(3,4,6-trichloro-2-{[2-(3-methylphenyl)ethoxy]carbonyl}phenyl)oxalate; bis(3,4,6-trichloro-2-{[2-(4-methylphenyl)ethoxy]carbonyl}phenyl)oxalate; bis{3,4,6-trichloro-2-[(2-phenylpropoxy)carbonyl]phenyl}oxalate; bis(3,4,6-trichloro-2-[(3-phenylpropoxy)carbonyl]phenyl}oxalate; bis{3,4,6-trichloro-2[1-naphthalenylmethoxy)carbonyl]phenyl}oxalate; bis{3,4,6-trichloro-2-[2-naphthalenylmethoxy)carbonyl]phenyl}oxalate; bis{3,4,6-trichloro-2-[(2,2-diphenylethoxy)carbonyl]phenyl}oxalate; bis{3,4,6-trichloro-2-[(9-fluorenylmethoxy)carbonyl]phenyl}oxalate; and bis{3,4,6-trichloro-2-[(9-anthracenylmethoxy)carbonyl]phenyl}oxalate.

In some embodiments, the at least one oxalate ester is present in an amount ranging from 3 percent to 60 percent by weight, based upon the total weight of the combined activator system and oxalate system.

In some embodiments, the at least one dye is a fluorescer selected from the group consisting of 1-methoxy-9,10-bis(phenylethynyl)anthracene, perylene, rubrene, 16,17-didecycloxyviolanthrone, 2-ethyl-9,10-bis(phenylethynyl)anthracene; 2-chloro-9,10-bis(4-ethoxyphenyl)anthracene; 2-chloro-9,10-bis(4-methoxyphenyl)anthracene; 9,10-bis(phenylethynyl)anthracene; 1-chloro-9,10-bis(phenylethynyl)anthracene; 1,8-dichloro-9,10-bis(phenylethynyl)anthracene; 1,5-dichloro-9,10-bis(phenylethynyl)anthracene; 2,3-dichloro-9,10-bis(phenylethynyl)anthracene; 5,12-bis(phenylethynyl)tetracene, 9,10-diphenylanthracene; 1,6,7,12-tetraphenoxy-N,N'-bis(2,6-diisopropylphenyl)-3,4,9,10-perylene dicarboximide; 1,6,7,12-tetraphenoxy-N,N' bis(2,5-di-t-butylphenyl)-3,4,9,10-perylene dicarboximide; 1,7-dichloro-6,12-diphenoxy-N,N'-bis(2,6-diisopropylphenyl)-3,4,9,10-perylene dicarboximide; 1,6,7,12-tetra(p-bromophenoxy)-N,N'-bis(2,6-diisopropylphenyl)-3,4,9,10-perylene dicarboximide; 1,6,7,12-tetraphenoxy-N,N' dineopentyl-3,4,9,10-perylene dicarboximide; 1,6,7,12-tetra-(p-t-butylphenoxy)-N,N'-dineopentyl-3,4,9,10-perylenedicarboximide; 1,6,7,12-tetra(o-chlorophenoxy)-N,N'-bis(2,6-diisopropylphenyl)-3,4,9,10-perylene dicarboximide; 1,6,7,12-tetra(p-chlorophenoxy)-N,N'-bis(2,6-diisopropylphenyl)-3,4,9,10-perylene dicarboximide; 1,6,7,12-tetra(o-fluorophenoxy)-N,N'-bis(2,6-diisopropylphenyl)-3,4,9,10-perylene dicarboximide; 1,6,7,12-tetra(p-fluorophenoxy)-N,N'-bis(2,6-diisopropylphenyl)-3,4,9,10-perylenedicarboximide; 1,6,7,12-tetraphenoxy-N,N'-diethyl-3,4,9,10-perylene dicarboximide; 1,7-dibromo-6,12-diphenoxy-N,N'-bis(2-isopropylphenyl)-3,4,9,10-perylene dicarboximide; 16,17-dihexyloxyviolanthrone; and 1,4-dimethyl-9,10-bis(phenylethynyl)anthracene.

In some embodiments, the at least one dye is a fluorescer present in an amount ranging from 0.05 percent to 0.9 percent by weight, based on the total weight of the oxalate system.

In some embodiments, the at least one first solvent is a low melting solvents selected from the group consisting of alkyl benzoates, dialkyl malonates, dialkyl dialkylmalonates, dialkyl arylalkylmalonates, dialkyl succinates, dialkyl glutarates, dialkyl adipates, dialkyl pimelates, dialkyl polyalkylmalonates, acetyl trialkyl citrates, 2-acetyloxy isobutyrates, paraffinic liquids, isoparaffinic liquids, toluene, and nitroethane.

In some embodiments, the at least one inorganic salt is selected from the group consisting of sodium thiosulphate, potassium thiosulphate, cobalt acetate, copper acetate, lead acetate, cupric chloride, ferric chloride, calcium iodide, potassium iodide, and silver nitrate.

In some embodiments, the at least one inorganic salt is present in an amount ranging from 0.05 percent to 30 percent by weight, based on the total weight of the oxalate system.

In some embodiments, the at least one peroxide is selected from the group consisting of hydrogen peroxide; sodium peroxide; sodium perborate; sodium pyrophosphate peroxide; urea peroxide; histidine peroxide; t-butylhydroperoxide; peroxybenzoic acid, and sodium percarbonate.

In some embodiments, the at least one peroxide is present in an amount ranging from 0.25 percent to 25 percent by weight, based on the total weight of the combined activator system and oxalate system.

In some embodiments, the at least one second solvent is selected from the group consisting of trialkyl citrates, dialkyl phthalates, glycols, and glycol ethers.

In some embodiments, the at least one catalyst is selected from the group consisting of dimethylbenzylamine, N,N-dimethyl-1-phenylethylamine, N-ethyl-N-methylbenzyl amine, diethylbenzylamine, N-methyl-N-propylbenzylamine, N,N-dibutylbenzylamine, N,N-bis(1-methylethyl)benzenemethanamine, methyl dibenzylamine, ethyl dibenzylamine, n-propyl dibenzylamine, iso-propyl dibenzylamine, butyl dibenzylamine, iso-butyl dibenzylamine, N,N-dibenzyl-2-phenylethanamine, hexyl dibenzylamine, tribenzylamine, 4-methyl-N,N-bis[(4-methylphenyl)methyl]benzenemethanamine, 4-methyl-N,N-bis(phenylmethyl)benzenemethanamine, N-methyl-N-phenylbenzenemethanamine, N-ethyl-N-phenylbenzenemethanamine, N,4-dimethyl-N-phenylbenzenemethanamine, N-propyl-N-phenylbenzenemethanamine, N,N-diphenylbenzenemethanamine, N,N-bis(4-methylphenyl)benzenemethanamine, lithium benzoate, sodium benzoate, potassium benzoate, cesium benzoate, lithium salicylate, sodium salicylate, potassium salicylate, cesium salicylate, lithium o-anisate, sodium o-anisate, potassium o-anisate, cesium o-anisate, lithium p-anisate, sodium p-anisate, potassium p-anisate, and/or cesium p-anisate, In some embodiments, the at least one catalyst is present at a concentration ranging from 5% to 0.0005% of the total weight of the activator system and oxalate system.

In some embodiments, the chemiluminescent system further includes a third solvent configured to dissolve the at least one catalyst and allow mixing of the at least one peroxide, wherein the third solvent is selected from the group consisting of aliphatic tertiary alcohols, chosen from, but not restricted to, tert-butanol, 3-methyl-3-pentanol, 2-methyl-2-butanol, ethyl 2-hydroxyisobutyrate, and methyl 2-hydroxyisobutyrate; glycols chosen from, but not restricted to ethylene glycol and propylene glycol; and glycol ethers chosen from, but not restricted to ethylene glycol monomethyl ether, ethylene glycol diethyl ether, ethylene glycol monobutyl ether, ethylene glycol dibutyl ether, and propylene glycol dimethyl ether.

In some embodiments, the third solvent is present in a concentration ranging from 0% to 90% based on the total weight of activator system.

In some embodiments, the broad temperature chemiluminescent system and method of the present invention is configured for use with munitions to produce useable light at a broad temperature range when activated.

In some embodiments, the system of the present invention, when activated, is configured to produce useable light in a temperature range of −110° C. to 75° C. In some embodiments, the components of the system of the present invention, when activated, are configured to produce useable light in a temperature range of −80° C. to 50° C. In some embodiments, the components of the system of the present invention, when activated, are configured to produce useable light in a temperature range of −110° C. to 50° C. In some embodiments, the components of the system of the present invention, when activated, are configured to produce useable light in a temperature range of −80° C. to 75° C. In some embodiments, the components of the system of the present invention, when activated, are configured to produce useable light in a temperature range of −30° C. to 30° C. In some embodiments, the components of the system of the present invention, when activated, are configured to produce useable light in a temperature range of −100° C. to 0° C. In some embodiments, the components of the system of the present invention, when activated, are configured to produce useable light in a temperature range of −20° C. to 75° C. In some embodiments, the components of the system of the present invention, when activated, are configured to produce useable light in a temperature down to −110° C. In some embodiments, the components of the system of the present invention, when activated, are configured to produce useable light in a temperature range of −60° C. to 20° C. In some embodiments, the components of the system of the present invention, when activated, are configured to produce useable light in a temperature range of −110° C. to −10° C.

In some embodiments, the system and method of the present invention may include, but are not limited to, at least one activator system combined with at least one oxalate system. Combining may include any suitable method of contacting one system with another system such as by mixing or equivalent. In some embodiments, the oxalate system may include, but is not limited to, an oxalate solution with at least one oxalate ester, at least one dye such as a fluorescer, at least one solvent, and/or at least one inorganic salt. In some embodiments, the activator system may include, but is not limited to, at least one catalyst, at least one peroxide, and/or at least one solvent such as a bridging solvent, if required, to allow sufficient mixing of the peroxide component, and at least one solvent such as a low melting solvent.

In some embodiments, the ratio of the weight of the oxalate system to the weight of the activator system ranges from 1:9 to 4:1. In some embodiments, the ratio of the weight of the oxalate system to the weight of the activator system ranges from 1:5 to 2:1. In some embodiments, the ratio of the weight of the oxalate system to the weight of the activator system ranges from 1:1 to 3:1. In some embodiments, the ratio of the weight of the oxalate system to the weight of the activator system ranges from 1:3 to 3:1. In some embodiments, the ratio of the weight of the oxalate system to the weight of the activator system ranges from 1:2 to 2:1. In some embodiments, the ratio of the weight of the oxalate system to the weight of the activator system ranges from 2:1 to 4:1. In some embodiments, the ratio of the weight of the oxalate system to the weight of the activator system ranges from 1:6 to 2:1. In some embodiments, the ratio of the weight of the oxalate system to the weight of the activator system ranges from 1:1 to 4:1.

In some embodiments, the ratio of the weight of the oxalate system to the weight of the activator system is 1:2. In some embodiments, the ratio of the weight of the oxalate system to the weight of the activator system is 2:1. In some embodiments, the ratio of the weight of the oxalate system to the weight of the activator system is 3:1. In some embodiments, the ratio of the weight of the oxalate system to the weight of the activator system is 1:8. In some embodiments, the ratio of the weight of the oxalate system to the weight of the activator system is 1:9. In some embodiments, the ratio of the weight of the oxalate system to the weight of the activator system is 4:1. In some embodiments, the ratio of the weight of the oxalate system to the weight of the activator system is 8:2. In some embodiments, the ratio of the weight of the oxalate system to the weight of the activator system is 1:5. In some embodiments, the ratio of the weight of the oxalate system to the weight of the activator system is 1:3.

In some embodiments, the at least one oxalate ester may include, but is not limited to, bis(2,4,5-trichloro-6-carbopentoxyphenyl)oxalate (CPPO); bis(2,4,5-trichlorophenyl)oxalate; bis(2,4,5-tribromo-6-carbohexoxyphenyl)oxalate; bis (2,4,5-trichloro-6-carboisopentoxyphenyl)oxalate; bis(2,4,5-trichloro-6-carbobenzoxyphenyl)oxalate; bis(2-nitrophenyl)oxalate; bis(2,4-dinitrophenyl)oxalate; bis(2,6-dichloro-4-nitrophenyl)oxalate; bis(2,4,6-trichlorophenyl)oxalate; bis(3-trifluoromethyl-4-nitrophenyl)oxalate; bis(2-methyl-4,6-dinitrophenyl)oxalate; bis(1,2-dimethyl-4,6-dinitrophenyl)oxalate; bis(2,4-dichlorophenyl)oxalate; bis (2,4-dinitrophenyl)oxalate; bis(2,5-dinitrophenyl)oxalate; bis(2-formyl-4-nitrophenyl)oxalate; bis(pentachlorophenyl)oxalate; bis(1,2-dihydro-2-oxo-1-pyridyl)glyoxal; bis(2,4-dinitro-6-methylphenyl)oxalate; and/or bis-N-phthalimidyl oxalate.

In some embodiments, the at least one oxalate ester may include, but is not limited to, oxalates represented by the general formula (I)

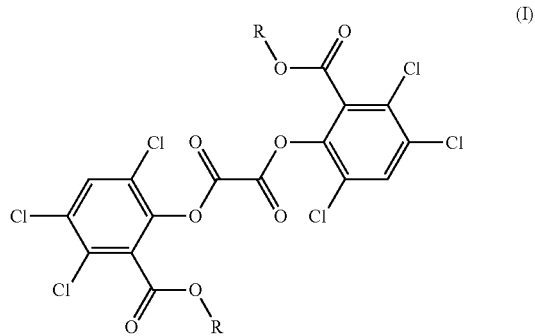

(I)

wherein R=CH$_2$A, and A is chosen from alkyl chains, alkyl rings, and aromatic rings or combinations thereof, and wherein R is linear or nonlinear, and comprises from 4-15 carbon atoms.

In some embodiments, the at least one oxalate ester may include, but is not limited to, bis{3,4,6-trichloro-2-[(2-methylpropoxy)carbonyl]phenyl}oxalate; bis{3,4,6-trichloro-2-[(cyclopropylmethoxy)carbonyl]phenyl}oxalate; bis{3,4,6-trichloro-2-[(2-methylbutoxy)carbonyl]phenyl}oxalate; bis{3,4,6-trichloro-2-[(3-methylbutoxy)carbonyl] phenyl}oxalate; bis{3,4,6-trichloro-2-[(2,2-dimethylpropoxy)carbonyl]phenyl}oxalate; bis{3,4,6-trichloro-2-[(2-methylpentyloxy)carbonyl]phenyl}oxalate; bis{3,4,6-trichloro-2-[(3-methylpentyloxy)carbonyl]phenyl}oxalate; bis{3,4,6-trichloro-2-[(4-methylpentyloxy)carbonyl] phenyl}oxalate; bis{3,4,6-trichloro-2-[(3,3-dimethylbutoxy) carbonyl]phenyl}oxalate; bis{3,4,6-trichloro-2-[(2-ethylbutoxy)carbonyl]phenyl}oxalate; bis{3,4,6-trichloro-2-[(cyclopentylmethoxy)carbonyl]phenyl}oxalate; bis{3,4,6-trichloro-2-[(2-methylhexyloxy)carbonyl]phenyl}oxalate; bis{3,4,6-trichloro-2-[(3-methylhexyloxy)carbonyl] phenyl}oxalate; bis{3,4,6-trichloro-2-[(4-methylhexyloxy) carbonyl]phenyl}oxalate; bis{3,4,6-trichloro-2-[(5-methylhexyloxy)carbonyl]phenyl}oxalate; bis{3,4,6-trichloro-2-[(cyclohexylmethoxy)carbonyl]phenyl}oxalate; bis{3,4,6-trichloro-2-[(phenylmethoxy)carbonyl]phenyl}oxalate; bis{3,4,6-trichloro-2-[(2-phenylethoxy)carbonyl] phenyl}oxalate; bis(3,4,6-trichloro-2-{[(2-methylphenyl) methoxy]carbonyl}phenyl)oxalate; bis(3,4,6-trichloro-2-{ [(3-methylphenyl)methoxy]carbonyl}phenyl)oxalate; bis(3, 4,6-trichloro-2-{[(4-methylphenyl)methoxy] carbonyl}phenyl)oxalate; bis(3,4,6-trichloro-2-{[(2,3-dimethylphenyl)methoxy]carbonyl}phenyl)oxalate; bis(3,4, 6-trichloro-2-{[(2,4-dimethylphenyl)methoxy] carbonyl}phenyl)oxalate; bis(3,4,6-trichloro-2-{[3,4-dimethylphenyl)methoxy]carbonyl}phenyl)oxalate; bis(3,4, 6-trichloro-2-{[(3,5-dimethylphenyl)methoxy] carbonyl}phenyl)oxalate; bis(3,4,6-trichloro-2-{[(2,6-dimethylphenyl)methoxy]carbonyl}phenyl)oxalate; bis(3,4, 6-trichloro-2-{[(2-ethylphenyl)methoxy]carbonyl}phenyl) oxalate; bis(3,4,6-trichloro-2-{[(3-ethylphenyl)methoxy] carbonyl}phenyl)oxalate; bis(3,4,6-trichloro-2-{[(4-ethylphenyl)methoxy]carbonyl}phenyl)oxalate; bis(3,4,6-trichloro-2-{[2-(2-methylphenyl)ethoxy]carbonyl}phenyl) oxalate; bis(3,4,6-trichloro-2-{[2-(3-methylphenyl)ethoxy] carbonyl}phenyl)oxalate; bis(3,4,6-trichloro-2-{[2-(4-methylphenyl)ethoxy]carbonyl}phenyl)oxalate; bis{3,4,6-trichloro-2-[(2-phenylpropoxy)carbonyl]phenyl}oxalate; bis (3,4,6-trichloro-2-[(3-phenylpropoxy)carbonyl] phenyl}oxalate; bis{3,4,6-trichloro-2[1-naphthalenylmethoxy)carbonyl]phenyl}oxalate; bis{3,4,6-trichloro-2-[2-naphthalenylmethoxy)carbonyl] phenyl}oxalate; bis{3,4,6-trichloro-2-[(2,2-diphenylethoxy) carbonyl]phenyl}oxalate; bis{3,4,6-trichloro-2-[(9-fluorenylmethoxy)carbonyl]phenyl}oxalate; and/or bis{3,4, 6-trichloro-2-[(9-anthracenylmethoxy)carbonyl] phenyl}oxalate.

In some embodiments, the at least one oxalate ester is present in an amount ranging from 3 percent to 60 percent by weight, based upon the total weight of the combined activator system and oxalate system. In some embodiments, the at least one oxalate ester is present in an amount ranging from 8 percent to 50 percent by weight, based upon the total weight of the combined activator system and oxalate system. In some embodiments, the at least one oxalate ester is present in an amount ranging from 15 percent to 60 percent by weight, based upon the total weight of the combined activator system and oxalate system. In some embodiments, the at least one oxalate ester is present in an amount ranging from 10 percent to 40 percent by weight, based upon the total weight of the combined activator system and oxalate system. In some embodiments, the at least one oxalate ester is present in an amount ranging from 3 percent to 30 percent by weight, based upon the total weight of the combined activator system and oxalate system. In some embodiments, the at least one oxalate ester is present in an amount ranging from 5 percent to 30 percent by weight, based upon the total weight of the combined activator system and oxalate system.

In some embodiments, the at least one oxalate ester is present in an amount ranging from 20 percent to 60 percent by weight, based upon the total weight of the combined activator system and oxalate system. In some embodiments, the at least one oxalate ester is present in an amount ranging from 40 percent to 60 percent by weight, based upon the total weight of the combined activator system and oxalate system. In some embodiments, the at least one oxalate ester is present in an amount ranging from 3 percent to 20 percent by weight, based upon the total weight of the combined activator system and oxalate system.

In some embodiments, the at least one oxalate ester is present at 3 percent by weight, based upon the total weight of the combined activator system and oxalate system. In some embodiments, the at least one oxalate ester is present at 60 percent by weight, based upon the total weight of the combined activator system and oxalate system. In some embodiments, the at least one oxalate ester is present at more than 3 percent by weight, based upon the total weight of the combined activator system and oxalate system.

In some embodiments, the at least oxalate ester is present at the weight percents and the weight percent ranges detailed above, based on the weight of the oxalate system.

In some embodiments, the at least one dye such as a fluorescer may include, but is not limited to, 1-methoxy-9,10-bis(phenylethynyl)anthracene, perylene, rubrene, 16,17-didecycloxyviolanthrone, 2-ethyl-9,10-bis(phenylethynyl)anthracene; 2-chloro-9,10-bis(4-ethoxyphenyl)anthracene; 2-chloro-9,10-bis(4-methoxyphenyl)anthracene; 9,10-bis(phenylethynyl)anthracene; 1-chloro-9,10-bis(phenylethynyl)anthracene; 1,8-dichloro-9,10-bis(phenylethynyl)anthracene; 1,5-dichloro-9,10-bis(phenylethynyl)anthracene; 2,3-dichloro-9,10-bis(phenylethynyl)anthracene; 5,12-bis(phenylethynyl)tetracene, 9,10-diphenylanthracene; 1,6,7,12-tetraphenoxy-N,N'-bis(2,6-diisopropylphenyl)-3,4,9,10-perylene dicarboximide; 1,6,7,12-tetraphenoxy-N,N' bis(2,5-di-t-butylphenyl)-3,4,9,10-perylene dicarboximide; 1,7-dichloro-6,12-diphenoxy-N,N'-bis(2,6-diisopropylphenyl)-3,4,9,10-perylene dicarboximide; 1,6,7,12-tetra(p-bromophenoxy)-N,N'-bis(2,6-diisopropylphenyl)-3,4,9,10-perylene dicarboximide; 1,6,7,12-tetraphenoxy-N,N' dineopentyl-3,4,9,10-perylene dicarboximide; 1,6,7,12-tetra-(p-t-butylphenoxy)-N,N'-dineopentyl-3,4,9,10-perylenedicarboximide; 1,6,7,12-tetra(o-chlorophenoxy)-N,N'-bis(2,6-diisopropylphenyl)-3,4,9,10-perylene dicarboximide; 1,6,7,12-tetra(p-chlorophenoxy)-N,N'-bis(2,6-diisopropylphenyl)-3,4,9,10-perylene dicarboximide; 1,6,7,12-tetra(o-fluorophenoxy)-N,N'-bis(2,6-diisopropylphenyl)-3,4,9,10-perylene dicarboximide; 1,6,7,12-tetra(p-fluorophenoxy)-N,N'-bis(2,6-diisopropylphenyl)-3,4,9,10-perylenedicarboximide; 1,6,7,12-tetraphenoxy-N,N'-diethyl-3,4,9,10-perylene dicarboximide; 1,7-dibromo-6,12-diphenoxy-N,N'-bis(2-isopropylphenyl)-3,4,9,10-perylene dicarboximide; 16,17-dihexyloxyviolanthrone; and/or 1,4-dimethyl-9,10-bis(phenylethynyl)anthracene.

In some embodiments, the at least one dye such as a fluorescer is present in an amount ranging from 0.05 percent to 0.9 percent by weight, based on the total weight of the combined activator system and oxalate system. In some embodiments, the at least one dye such as a fluorescer is present in an amount ranging from 0.1 percent to 0.8 percent by weight, based on the total weight of the combined activator system and oxalate system. In some embodiments, the at least one dye such as a fluorescer is present in an amount ranging from 0.15 percent to 0.9 percent by weight, based on the total weight of the combined activator system and oxalate system. In some embodiments, the at least one dye such as a fluorescer is present in an amount ranging from 0.05 percent to 0.5 percent by weight, based on the total weight of the combined activator system and oxalate system. In some embodiments, the at least one dye such as a fluorescer is present in an amount ranging from 0.2 percent to 0.7 percent by weight, based on the total weight of the combined activator system and oxalate system. In some embodiments, the at least one dye such as a fluorescer is present in an amount ranging from 0.05 percent to 0.1 percent by weight, based on the total weight of the combined activator system and oxalate system. In some embodiments, the at least one dye such as a fluorescer is present in an amount ranging from 0.05 percent to 0.3 percent by weight, based on the total weight of the combined activator system and oxalate system.

In some embodiments, the at least one dye such as a fluorescer is present at 0.05 percent by weight, based on the total weight of the combined activator system and oxalate system. In some embodiments, the at least one dye such as a fluorescer is present at 0.2 percent by weight, based on the total weight of the combined activator system and oxalate system. In some embodiments, the at least one dye such as a fluorescer is present at 0.5 percent by weight, based on the total weight of the combined activator system and oxalate system. In some embodiments, the at least one dye such as a fluorescer is present at 0.9 percent by weight, based on the total weight of the combined activator system and oxalate system.

In some embodiments, the at least one dye such as a fluorescer is present at the weight percents and the weight percent ranges detailed above, based on the weight of the oxalate system.

In some embodiments, the at least one solvent of the oxalate system may include, but is not limited to low melting solvents. In some embodiments, the at least one solvent of the oxalate system may include, but is not limited to, alkyl benzoates, dialkyl malonates, dialkyl dialkylmalonates, dialkyl arylalkylmalonates, dialkyl succinates, dialkyl glutarates, dialkyl adipates, dialkyl pimelates, dialkyl polyalkylmalonates, acetyl trialkyl citrates, 2-acetyloxy isobutyrates, paraffinic liquids, isoparaffinic liquids, toluene, nitroethane, and/or any combination thereof.

In some embodiments, the at least one first solvent is present in an amount ranging from 10 percent to 97 percent of the total weight of the oxalate system. In some embodiments, the at least one first solvent is present in an amount ranging from 20 percent to 80 percent of the total weight of the oxalate system. In some embodiments, the at least one first solvent is present in an amount ranging from 10 percent to 75 percent of the total weight of the oxalate system. In some embodiments, the at least one first solvent is present in an amount ranging from 30 percent to 80 percent of the total weight of the oxalate system. In some embodiments, the at least one first solvent is present in an amount ranging from 15 percent to 50 percent of the total weight of the oxalate system. In some embodiments, the at least one first solvent is present in an amount ranging from 50 percent to 97 percent of the total weight of the oxalate system. In some embodiments, the at least one first solvent is present in an amount ranging from 70 percent to 97 percent of the total weight of the oxalate system.

In some embodiments, the at least one first solvent is present at 10 percent of the total weight of the oxalate system. In some embodiments, the at least one first solvent is present at 40 percent of the total weight of the oxalate system. In some embodiments, the at least one first solvent is present at 60 percent of the total weight of the oxalate system. In some embodiments, the at least one first solvent is present at 75 percent of the total weight of the oxalate system. In some embodiments, the at least one first solvent is present at 97 percent of the total weight of the oxalate system.

In some embodiments, the at least one second solvent is present in an amount ranging from 10 percent to 97 percent of the total weight of the oxalate system. In some embodiments, the at least one second solvent is present in an amount ranging from 20 percent to 80 percent of the total weight of the oxalate system. In some embodiments, the at least one second solvent is present in an amount ranging from 10 percent to 75 percent of the total weight of the oxalate system. In some embodiments, the at least one second solvent is present in an amount ranging from 30 percent to 80 percent of the total weight of the oxalate system. In some embodiments, the at least one second solvent is present in an amount ranging from 15 percent to 50 percent of the total weight of the oxalate system. In some embodiments, the at least one second solvent is present in an amount ranging from 50 percent to 97 percent of the total weight of the oxalate system. In some embodiments, the at least one second solvent is present in an amount ranging from 70 percent to 97 percent of the total weight of the oxalate system.

In some embodiments, the at least one second solvent is present at 10 percent of the total weight of the oxalate system. In some embodiments, the at least one second solvent is present at 40 percent of the total weight of the oxalate system. In some embodiments, the at least one second solvent is present at 60 percent of the total weight of the oxalate system. In some embodiments, the at least one second solvent is present at 75 percent of the total weight of the oxalate system. In some embodiments, the at least one second solvent is present at 97 percent of the total weight of the oxalate system.

In some embodiments, the at least one inorganic salt may include, but is not limited to, sodium thiosulphate, potassium thiosulphate, cobalt acetate, copper acetate, lead acetate, cupric chloride, ferric chloride, calcium iodide, potassium iodide, and/or silver nitrate.

In some embodiments, the at least one inorganic salt is present in an amount ranging from 0.05 percent to 30 percent by weight, based on the total weight of the combined activator system and oxalate system. In some embodiments, the at least one inorganic salt is present in an amount ranging from 0.5 percent to 25 percent by weight, based on the total weight of the combined activator system and oxalate system. In some embodiments, the at least one inorganic salt is present in an amount ranging from 5 percent to 20 percent by weight, based on the total weight of the combined activator system and oxalate system. In some embodiments, the at least one inorganic salt is present in an amount ranging from 10 percent to 15 percent by weight, based on the total weight of the combined activator system and oxalate system. In some embodiments, the at least one inorganic salt is present in an amount ranging from 1 percent to 20 percent by weight, based on the total weight of the combined activator system and oxalate system. In some embodiments, the at least one inorganic salt is present in an amount ranging from 0.05 percent to 10 percent by weight, based on the total weight of the combined activator system and oxalate system. In some embodiments, the at least one inorganic salt is present in an amount ranging from 0.1 percent to 5 percent by weight, based on the total weight of the combined activator system and oxalate system.

In some embodiments, the at least one inorganic salt is present at 0.05 percent by weight, based on the total weight of the combined activator system and oxalate system. In some embodiments, the at least one inorganic salt is present at 30 percent by weight, based on the total weight of the combined activator system and oxalate system. In some embodiments, the at least one inorganic salt is present at 20 percent by weight, based on the total weight of the combined activator system and oxalate system. In some embodiments, the at least one inorganic salt is present at 15 percent by weight, based on the total weight of the combined activator system and oxalate system. In some embodiments, the at least one inorganic salt is present at 1 percent by weight, based on the total weight of the combined activator system and oxalate system. In some embodiments, the at least one inorganic salt is present at 2 percent by weight, based on the total weight of the combined activator system and oxalate system. In some embodiments, the at least one inorganic salt is present at 5 percent by weight, based on the total weight of the combined activator system and oxalate system.

In some embodiments, the at least one inorganic salt is present at the weight percents and the weight percent ranges detailed above, based on the weight of the oxalate system.

In some embodiments, the at least one peroxide may include, but is not limited to, hydrogen peroxide; sodium peroxide; sodium perborate; sodium pyrophosphate peroxide; urea peroxide; histidine peroxide; t-butylhydroperoxide; peroxybenzoic acid, and/or sodium percarbonate.

In some embodiments, the at least one peroxide is present in an amount ranging from 0.25 percent to 25 percent by weight, based on the total weight of the combined activator system and oxalate system. In some embodiments, the at least one peroxide is present in an amount ranging from 5 percent to 25 percent by weight, based on the total weight of the combined activator system and oxalate system. In some embodiments, the at least one peroxide is present in an amount ranging from 1 percent to 20 percent by weight, based on the total weight of the combined activator system and oxalate system. In some embodiments, the at least one peroxide is present in an amount ranging from 10 percent to 15 percent by weight, based on the total weight of the combined activator system and oxalate system. In some embodiments, the at least one peroxide is present in an amount ranging from 0.25 percent to 5 percent by weight, based on the total weight of the combined activator system and oxalate system.

In some embodiments, the at least one peroxide is present at 0.25 percent by weight, based on the total weight of the combined activator system and oxalate system. In some embodiments, the at least one peroxide is present at 1 percent by weight, based on the total weight of the combined activator system and oxalate system. In some embodiments, the at least one peroxide is present at 5 percent by weight, based on the total weight of the combined activator system and oxalate system. In some embodiments, the at least one peroxide is present at 10 percent by weight, based on the total weight of the combined activator system and oxalate system. In some embodiments, the at least one peroxide is present at 20 percent by weight, based on the total weight of the combined activator system and oxalate system. In some embodiments, the at least one peroxide is present at 25 percent by weight, based on the total weight of the combined activator system and oxalate system.

In some embodiments, the at least one peroxide is present at the weight percents and the weight percent ranges detailed above, based on the weight of the activator system.

In some embodiments, the at least one solvent of the activator system may include, but is not limited to low melting solvents. In some embodiments, the at least one solvent of the activator system may include, but is not limited to, trialkyl citrates, dialkyl phthalates, glycols, glycol ethers and any combination thereof.

In some embodiments, the at least one third solvent is present in an amount ranging from 0 percent to 95 percent of the total weight of the activator system. In some embodiments, the at least one third solvent is present in an amount ranging from 10 percent to 80 percent of the total weight of the activator system. In some embodiments, the at least one third solvent is present in an amount ranging from 10 percent to 60 percent of the total weight of the activator system. In some embodiments, the at least one third solvent is present in an amount ranging from 30 percent to 90 percent of the total weight of the activator system. In some embodiments, the at least one third solvent is present in an amount ranging from 15 percent to 90 percent of the total weight of the activator system. In some embodiments, the at least one third solvent is present in an amount ranging from 50 percent to 95 percent of the total weight of the activator system. In some embodiments, the at least one third solvent is present in an amount ranging from 0 percent to 10 percent of the total weight of the activator system.

In some embodiments, the at least one third solvent is present at 0 percent of the total weight of the activator system. In some embodiments, the at least one third solvent is present at 20 percent of the total weight of the activator system. In some embodiments, the at least one third solvent is present at 40 percent of the total weight of the activator system. In some embodiments, the at least one third solvent is present at 60 percent of the total weight of the activator system. In some embodiments, the at least one third solvent is present at 95 percent of the total weight of the activator system.

In some embodiments, the at least one fourth solvent is present in an amount ranging from 0 percent to 95 percent of the total weight of the activator system. In some embodiments, the at least one fourth solvent is present in an amount ranging from 10 percent to 80 percent of the total weight of the activator system. In some embodiments, the at least one fourth solvent is present in an amount ranging from 10 percent to 60 percent of the total weight of the activator system. In some embodiments, the at least one fourth solvent is present in an amount ranging from 30 percent to 90 percent of the total weight of the activator system. In some embodiments, the at least one fourth solvent is present in an amount ranging from 15 percent to 90 percent of the total weight of the activator system. In some embodiments, the at least one fourth solvent is present in an amount ranging from 50 percent to 95 percent of the total weight of the activator system. In some embodiments, the at least one fourth solvent is present in an amount ranging from 0 percent to 10 percent of the total weight of the activator system.

In some embodiments, the at least one fourth solvent is present at 0 percent of the total weight of the activator system. In some embodiments, the at least one fourth solvent is present at 20 percent of the total weight of the activator system. In some embodiments, the at least one fourth solvent is present at 40 percent of the total weight of the activator system. In some embodiments, the at least one fourth solvent is present at 60 percent of the total weight of the activator system. In some embodiments, the at least one fourth solvent is present at 95 percent of the total weight of the activator system.

In some embodiments, the at least one catalyst may include, but is not limited to, dimethylbenzylamine, N,N-dimethyl-1-phenylethylamine, N-ethyl-N-methylbenzylamine, diethylbenzylamine, N-methyl-N-propylbenzylamine, N,N-dibutylbenzylamine, N,N-bis(1-methylethyl)benzenemethanamine, methyl dibenzylamine, ethyl dibenzylamine, n-propyl dibenzylamine, iso-propyl dibenzylamine, butyl dibenzylamine, iso-butyl dibenzylamine, N,N-dibenzyl-2-phenylethanamine, hexyl dibenzylamine, tribenzylamine, 4-methyl-N,N-bis[(4-methylphenyl)methyl]benzenemethanamine, 4-methyl-N,N-bis(phenylmethyl)benzenemethanamine, N-methyl-N-phenylbenzenemethanamine, N-ethyl-N-phenylbenzenemethanamine, N,4-dimethyl-N-phenylbenzenemethanamine, N-propyl-N-phenylbenzenemethanamine, N,N-diphenylbenzenemethanamine, N,N-bis(4-methylphenyl)benzenemethanamine, lithium benzoate, sodium benzoate, potassium benzoate, cesium benzoate, lithium salicylate, sodium salicylate, potassium salicylate, cesium salicylate, lithium o-anisate, sodium o-anisate, potassium o-anisate, cesium o-anisate, lithium p-anisate, sodium p-anisate, potassium p-anisate, and/or cesium p-anisate.

In some embodiments, the at least one catalyst is present at a concentration ranging from 5% to 0.0005% by weight, based on the total weight of the combined activator system and oxalate system. In some embodiments, the at least one catalyst is present at a concentration ranging from 2% to 0.1% by weight, based on the total weight of the combined activator system and oxalate system. In some embodiments, the at least one catalyst is present at a concentration ranging from 1% to 0.0005% by weight, based on the total weight of the combined activator system and oxalate system. In some embodiments, the at least one catalyst is present at a concentration ranging from 5% to 2% by weight, based on the total weight of the combined activator system and oxalate system. In some embodiments, the at least one catalyst is present at a concentration ranging from 0.7% to 0.0005% by weight, based on the total weight of the combined activator system and oxalate system. In some embodiments, the at least one catalyst is present at a concentration ranging from 0.5% to 0.05% by weight, based on the total weight of the combined activator system and oxalate system. In some embodiments, the at least one catalyst is present at a concentration ranging from 5% to 3% by weight, based on the total weight of the combined activator system and oxalate system.

In some embodiments, the at least one catalyst is present at 5% by weight, based on the total weight of the combined activator system and oxalate system. In some embodiments, the at least one catalyst is present at 0.5% by weight, based on the total weight of the combined activator system and oxalate system. In some embodiments, the at least one catalyst is present at 0.05% by weight, based on the total weight of the combined activator system and oxalate system. In some embodiments, the at least one catalyst is present at 0.005% by weight, based on the total weight of the combined activator system and oxalate system. In some embodiments, the at least one catalyst is present at 0.0005% by weight, based on the total weight of the combined activator system and oxalate system. In some embodiments, the at least one catalyst is present at 2% by weight, based on the total weight of the combined activator system and oxalate system. In some embodiments, the at least one catalyst is present at 3% by weight, based on the total weight of the combined activator system and oxalate system.

In some embodiments, the at least one catalyst is present at the weight percents and the weight percent ranges detailed above, based on the weight of the activator system.

In some embodiments, the at least one catalyst is dissolved in a solvent. In some embodiments, the solvent may include at least one bridging solvent suitable to allow sufficient mixing of the peroxide. In some embodiments, the solvent may include, but is not limited to, aliphatic tertiary alcohols, chosen from, but not restricted to, tert-butanol, 3-methyl-3-pentanol, 2-methyl-2-butanol, ethyl 2-hydroxyisobutyrate, and methyl 2-hydroxyisobutyrate; glycols chosen from, but not restricted to ethylene glycol and propylene glycol; and glycol ethers chosen from, but not restricted to ethylene glycol monomethyl ether, ethylene glycol diethyl ether, ethylene glycol monobutyl ether, ethylene glycol dibutyl ether, and propylene glycol dimethyl ether or any combination thereof.

In some embodiments, the at least one solvent is present in an amount ranging from 0 percent to 95 percent of the total weight of the activator system. In some embodiments, the at least one solvent is present in an amount ranging from 10 percent to 80 percent of the total weight of the activator system. In some embodiments, the at least one solvent is present in an amount ranging from 10 percent to 60 percent of the total weight of the activator system. In some embodiments, the at least one solvent is present in an amount ranging from 30 percent to 90 percent of the total weight of the activator system. In some embodiments, the at least one solvent is present in an amount ranging from 15 percent to 90 percent of the total weight of the activator system. In some embodiments, the at least one solvent is present in an amount ranging from 50 percent to 95 percent of the total weight of the activator system. In some embodiments, the at least one solvent is present in an amount ranging from 0 percent to 10 percent of the total weight of the activator system.

In some embodiments, the at least one solvent is present at 0 percent of the total weight of the activator system. In some embodiments, the at least one solvent is present at 20 percent of the total weight of the activator system. In some embodiments, the at least one solvent is present at 40 percent of the total weight of the activator system. In some embodiments, the at least one solvent is present at 60 percent of the total weight of the activator system. In some embodiments, the at least one solvent is present at 95 percent of the total weight of the activator system.

Non-Limiting Example 1

The experiments in Table I illustrate the effect of changing catalyst ratios on the light output of a low temperature formulated oxalate ester. The Oxalate A was made from a mixture of 14% bis(2,4,5-trichloro-6-carbopentoxyphenyl)oxalate (CPPO) and 0.31% rubrene in a solvent made from 50% butyl benzoate and 50% diethyl diethyl malonate. Activator A was composed of 0.1% sodium salicylate and 0.05% tribenzylamine with 10% of a 50% aqueous hydrogen peroxide solution in a solvent mixture of 80% triethyl citrate and 20% methyl 2-hydroxyisobutyrate. Activator B was composed of 0.05% sodium salicylate and 0.05% tribenzyl amine with 10% of a 50% aqueous hydrogen peroxide solution in a solvent mixture of 80% triethyl citrate and 20% methyl 2-hydroxyisobutyrate. Activator C was composed of 0.005% sodium salicylate and 0.05% tribenzylamine with 10% of a 50% aqueous hydrogen peroxide solution in a solvent mixture of 80% triethyl citrate and 20% methyl 2-hydroxyisobutyrate. The tests were conducted measuring the light output with an ILT 1700 light meter. The reaction vessel was placed into the high speed mixer, then 1.8 g of the oxalate ester was added and the mixer was turned on and 4.0 g of the activator solution added. The results are shown in Table I.

TABLE I

[Adjustment of light output profile with multiple catalyst ratio.]

| Seconds | Activator A (lux) | Activator B (lux) | Activator C (lux) |
|---|---|---|---|
| 1.0 | 178 | 178 | 177 |
| 1.5 | 18390 | 18140 | 8127 |
| 2 | 11055 | 13660 | 7763 |
| 2.5 | 7850 | 10430 | 7393 |
| 3 | 5635 | 8130 | 7043 |
| 3.5 | 4080 | 6400 | 6703 |
| 4 | 2975 | 5075 | 6387 |
| 4.5 | 2197 | 4050 | 6093 |
| 5 | 1636 | 3270 | 5800 |
| 5.5 | 1235 | 2655 | 5557 |
| 6 | 945 | 2170 | 5333 |
| 6.5 | 730 | 1790 | 5087 |
| 7 | 570 | 1487 | 4883 |
| 7.5 | 450 | 1240 | 4703 |
| 8 | 357 | 1039 | 4513 |
| 8.5 | 286 | 875 | 4323 |
| 9 | 230 | 739 | 4167 |
| 9.5 | 188 | 629 | 4007 |
| 10 | 155 | 536 | 3860 |
| 10.5 | 128 | 460 | 3713 |
| 11 | 108 | 395 | 3583 |
| 11.5 | 91 | 343 | 3463 |
| 12 | 77 | 298 | 3337 |
| 12.5 | 66 | 259 | 3223 |
| 13 | 57 | 228 | 3117 |
| 13.5 | 49 | 200 | 3007 |
| 14 | 43 | 177 | 2917 |
| 14.5 | 38 | 156 | 2823 |
| 15 | 33 | 139 | 2740 |

Non-Limiting Example 2

A reaction vessel was placed in a high speed mixer and 200 mg of sodium thiosulfate was added to the cup. Oxalate A was reacted with Activator C at three different temperatures in the same fashion with both solutions maintained at the indicated temperature for at least 1 hour before combining and reacted as described in Example 1. The results are shown in FIG. 1. FIG. 1 represents the chemical light output of Oxalate A and Activator C at room temperature, 50 degrees C., and −50 degrees C.

In some embodiments, the present invention is a chemiluminescent system, including: an oxalate system, including: (a) at least one oxalate ester in an amount ranging from 3 to 60 percent by weight based on a total weight of the oxalate system, (b) at least one first solvent selected from the group consisting of: alkyl benzoates, dialkyl phthalates, trialkyl acetylcitrates, 2-acetyloxy isobutyrates, paraffinic liquids, isoparaffinic liquids, toluene, nitroethane, and a combination thereof, where the at least one first solvent is present in an amount ranging from 10 to 97 percent by weight based on the total weight of the oxalate system; (c) at least one second solvent selected from the group consisting of: dialkyl malonates, dialkyl dialkylmalonates, dialkyl arylalkylmalonates, dialkyl succinates, dialkyl glutarates, dialkyl adipates, dialkyl pimelates, dialkyl polyalkylmalonates and a combination thereof, where the at least one second solvent is present in an amount ranging from 5 to 85 percent by weight based on the total weight of the oxalate system; (d) at least one fluorescer, and (e) at least one inorganic salt, in an amount ranging from 0.1 to 30 percent by weight based on the total weight of the oxalate system, and an activator system, including: (a) at least one peroxide, (b) at least one third solvent selected from the group consisting of: tert-butanol, 3-methyl-3-pentanol, 2-methyl-2-butanol, ethyl 2-hydroxyisobutyrate, methyl 2-hydroxyisobutyrate, ethylene glycol, propylene glycol, ethylene glycol monomethyl ether, ethylene glycol diethyl ether, ethylene glycol monobutyl ether, ethylene glycol dibutyl ether, and propylene glycol dimethyl ether, and a combination thereof; where the at least one third solvent is present in an amount ranging from 5 to 85 percent by weight based on the total weight of the activator system, (c) at least one fourth solvent selected from the group consisting of: trialkyl citrates, dialkyl phthalates, glycols, glycol ethers, and a combination thereof; where the at least one fourth solvent is present in an amount ranging from 15 to 95 percent by weight based on a total weight of the activator system, and (d) at least one catalyst, and where the chemiluminescent system, at a temperature ranging from −110 degrees Celsius to 75 degrees Celsius, is configured to produce a light having an illuminescence.

In some embodiments, the at least one oxalate ester is represented by formula (I):

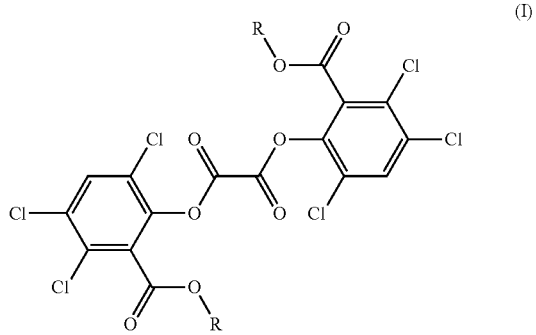

where $R=CH_2A$, and A is selected from the group consisting of an alkyl chain, alkyl ring, an aromatic ring, and a combination thereof, where R is linear or branched, and where R is from $C_{4-15}$.

In some embodiments, the at least one oxalate ester is selected from the group consisting of: bis{3,4,6-trichloro-2-[(2-methylpropoxy)carbonyl]phenyl}oxalate, bis{3,4,6-trichloro-2-[(cyclopropylmethoxy)carbonyl]phenyl}oxalate, bis{3,4,6-trichloro-2-[(2-methylbutoxy)carbonyl]phenyl}oxalate, bis{3,4,6-trichloro-2-[(3-methylbutoxy)carbonyl]phenyl}oxalate, bis{3,4,6-trichloro-2-[(2,2-dimethylpropoxy)carbonyl]phenyl}oxalate, bis{3,4,6-trichloro-2-[(2-methylpentyloxy)carbonyl]phenyl}oxalate, bis{3,4,6-trichloro-2-[(3-methylpentyloxy)carbonyl]phenyl}oxalate, bis{3,4,6-tri chloro-2-[(4-methylpentyloxy)carbonyl]phenyl}oxalate, bis{3,4,6-trichloro-2-[(3,3-dimethylbutoxy)carbonyl]phenyl}oxalate, bis{3,4,6-trichloro-2-[(2-ethylbutoxy)carbonyl]phenyl}oxalate, bis{3,4,6-trichloro-2-[(cyclopentylmethoxy)carbonyl]phenyl}oxalate, bis{3,4,6-trichloro-2-[(2-methylhexyloxy)carbonyl]phenyl}oxalate, bis{3,4,6-trichloro-2-[(3-methylhexyloxy)carbonyl]phenyl}oxalate, bis{3,4,6-trichloro-2-[(4-methylhexyloxy)carbonyl]phenyl}oxalate, bis{3,4,6-trichloro-2-[(5-methylhexyloxy)carbonyl]phenyl}oxalate, bis{3,4,6-trichloro-2-[(cyclohexylmethoxy)carbonyl]phenyl}oxalate, bis{3,46-trichloro-2-[(phenylmethoxy)carbonyl]phenyl}oxalate, bis{3,4,6-trichloro-2-[(2-phenylethoxy)carbonyl]phenyl}oxalate, bis(3,4,6-trichloro-2-{[(2-methylphenyl)methoxy]carbonyl}phenyl)oxalate, bis(3,4,6-trichloro-2-{[(3-methylphenyl)methoxy]carbonyl}phenyl)oxalate, bis(3,4,6-trichloro-2-{[(4-methylphenyl)methoxy]carbonyl}phenyl)oxalate, bis(3,4,6-trichloro-2-{[(2,3-dimethylphenyl)methoxy]carbonyl}phenyl)oxalate, bis(3,4,6-trichloro-2-{[(2,4-dimethylphenyl)methoxy]carbonyl}phenyl)oxalate, bis(3,4,6-trichloro-2-{[3,4-dimethylphenyl)methoxy]carbonyl}phenyl)oxalate, bis(3,4,6-trichloro-2-{[(3,5-dimethylphenyl)methoxy]carbonyl}phenyl)oxalate, bis(3,4,6-trichloro-2-{[(2,6-dimethylphenyl)methoxy]carbonyl}phenyl)oxalate, bis(3,4,6-trichloro-2-{[(2-ethylphenyl)methoxy]carbonyl}phenyl)oxalate, bis(3,4,6-trichloro-2-{[(3-ethylphenyl)methoxy]carbonyl}phenyl)oxalate, bis(3,4,6-trichloro-2-{[(4-ethylphenyl)methoxy]carbonyl}phenyl)oxalate, bis(3,4,6-trichloro-2-{[2-(2-methylphenyl)ethoxy]carbonyl}phenyl)oxalate, bis(3,4,6-trichloro-2-{[2-(3-methylphenyl)ethoxy]carbonyl}phenyl)oxalate, bis(3,4,6-trichloro-2-{[2-(4-methylphenyl)ethoxy]carbonyl}phenyl)oxalate, bis{3,4,6-trichloro-2-[(2-phenylpropoxy)carbonyl]phenyl}oxalate, bis{3,4,6-trichloro-2-[(3-phenylpropoxy)carbonyl]phenyl}oxalate, bis{3,4,6-trichloro-2-[1-naphthalenylmethoxy)carbonyl]phenyl}oxalate, bis{3,4,6-trichloro-2-[2-naphthalenylmethoxy)carbonyl]phenyl}oxalate, bis{3,4,6-trichloro-2-[(2,2-diphenylethoxy)carbonyl]phenyl}oxalate, bis{3,4,6-trichloro-2-[(9-fluorenylmethoxy)carbonyl]phenyl}oxalate, and bis{3,4,6-trichloro-2-[(9-anthracenylmethoxy)carbonyl]phenyl}oxalate.

In some embodiments, the at least one fluorescer is present in an amount ranging from 0.05 to 0.9 percent by weight based on the total weight of the chemiluminescent system.

In some embodiments, the at least one inorganic salt is selected from the group consisting of sodium thiosulphate, potassium thiosulphate, cobalt acetate, copper acetate, lead acetate, cupric chloride, ferric chloride, calcium iodide, potassium iodide, silver nitrate, and a combination thereof.

In some embodiments, the at least one peroxide is selected from the group consisting of hydrogen peroxide, sodium peroxide, sodium perborate, sodium pyrophosphate peroxide, urea peroxide, histidine peroxide, t-butylhydroperoxide, peroxynehzoic acid, sodium percarbonate, and a combination thereof.

In some embodiments, the at least one peroxide is present in an amount ranging from 0.25 to 25 percent by weight based on the total weight of the chemiluminescent system.

In some embodiments, the at least one catalyst is selected from the group consisting of: dimethylbenzylamine, N,N-dimethyl-1-phenylethylamine, N-ethyl-N-methylbenzyl amine, diethylbenzylamine, N-methyl-N-propylbenzylamine, N,N-dibutylbenzylamine, N,N-bis(1-methylethyl) benzenemethanamine, methyl dibenzylamine, ethyl dibenzylamine, n-propyl dibenzylamine, iso-propyl dibenzylamine, butyl dibenzylamine, iso-butyl dibenzylamine, N,N-dibenzyl-2-phenylethanamine, hexyl dibenzylamine, tribenzylamine, 4-methyl-N,N-bis[(4-methylphenyl)methyl]benzenemethanamine, 4-methyl-N,N-bis(phenylmethyl) benzenemethanamine, N-methyl-N-phenylbenzenemethanamine, N-ethyl-N-phenylbenzenemethanamine, N,4-dimethyl-N-phenylbenzenemethanamine, N-propyl-N-phenylbenzenemethanamine, N,N-diphenylbenzenemethanamine, N,N-bis(4-methylphenyl) benzenemethanamine, lithium benzoate, sodium benzoate, potassium benzoate, cesium benzoate, lithium salicylate, sodium salicylate, potassium salicylate, cesium salicylate, lithium o-anisate, sodium o-anisate, potassium o-anisate, cesium o-anisate, lithium p-anisate, sodium p-anisate, potassium p-anisate, and/or cesium p-anisate.

In some embodiments, the at least one catalyst is present in an amount ranging from 5 to 0.0005 percent by weight based on the total weight of the chemiluminescent system.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

What is claimed is:

1. A chemiluminescent system, comprising:
    an oxalate system, comprising:
        (a) at least one oxalate ester in an amount ranging from 3 to 60 percent by weight based on a total weight of the oxalate system,
        (b) at least one first solvent selected from the group consisting of: alkyl benzoates, dialkyl phthalates, trialkyl acetylcitrates, 2-acetyloxy isobutyrates, paraffinic liquids, isoparaffinic liquids, toluene, nitroethane, and a combination thereof,
            wherein the at least one first solvent is present in an amount ranging from 10 to 97 percent by weight based on the total weight of the oxalate system;
        (c) at least one second solvent selected from the group consisting of: dialkyl malonates, dialkyl dialkylmalonates, dialkyl arylalkylmalonates, dialkyl succinates, dialkyl glutarates, dialkyl adipates, dialkyl pimelates, dialkyl polyalkylmalonates, and a combination thereof,
            wherein the at least one second solvent is present in an amount ranging from 5 to 85 percent by weight based on the total weight of the oxalate system;
        (d) at least one fluorescer, and
        (e) at least one inorganic salt, in an amount ranging from 0.1 to 30 percent by weight based on the total weight of the oxalate system, and
    an activator system, comprising:
        (a) at least one peroxide,
        (b) at least one third solvent selected from the group consisting of: tert-butanol, 3-methyl-3-pentanol, 2-methyl-2-butanol, ethyl 2-hydroxyisobutyrate, methyl 2-hydroxyisobutyrate, ethylene glycol, propylene glycol, ethylene glycol monomethyl ether, ethylene glycol diethyl ether, ethylene glycol monobutyl ether, ethylene glycol dibutyl ether, and propylene glycol dimethyl ether, and a combination thereof;
            wherein the at least one third solvent is present in an amount ranging from 5 to 85 percent by weight based on the total weight of the activator system,
        (c) at least one fourth solvent selected from the group consisting of: trialkyl citrates, dialkyl phthalates, glycols, glycol ethers, and a combination thereof;
            wherein the at least one fourth solvent is present in an amount ranging from 15 to 95 percent by weight based on a total weight of the activator system, and
        (d) at least one catalyst, and
    wherein the chemiluminescent system, at a temperature ranging from −110 degrees Celsius to 75 degrees Celsius, is configured to produce a light having an illuminescence.

2. The chemiluminescent system of claim 1, wherein the at least one oxalate ester is represented by formula (I):

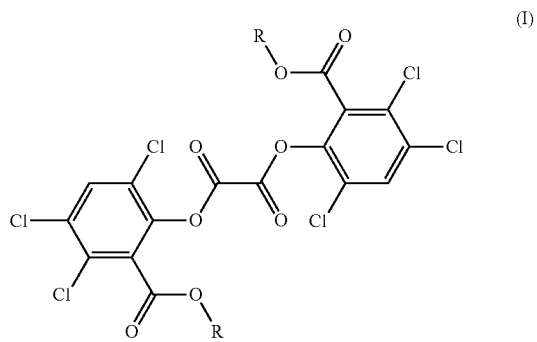

wherein R=CH$_2$A, and A is selected from the group consisting of an alkyl chain, alkyl ring, an aromatic ring, and a combination thereof,
wherein R is linear or branched, and
wherein R is from C$_{4-15}$.

3. The chemiluminescent system of claim 1, wherein the at least one oxalate ester is selected from the group consisting of: bis{3,4,6-trichloro-2-[(2-methylpropoxy)carbonyl]phenyl}oxalate, bis{3,4,6-trichloro-2-[(cyclopropylmethoxy)carbonyl]phenyl}oxalate, bis{3,4,6-trichloro-2-[(2-methylbutoxy)carbonyl]phenyl}oxalate, bis{3,4,6-trichloro-2-[(3-methylbutoxy)carbonyl]phenyl}oxalate, bis{3,4,6-trichloro-2-[(2,2-dimethylpropoxy)carbonyl]phenyl}oxalate, bis{3,4,6-trichloro-2-[(2-methylpentyloxy)carbonyl]phenyl}oxalate, bis{3,4,6-trichloro-2-[(3-methylpentyloxy)carbonyl]phenyl}oxalate, bis{3,4,6-tri chloro-2-[(4-methylpentyloxy)carbonyl]phenyl}oxalate, bis{3,4,6-trichloro-2-[(3,3-dimethylbutoxy)carbonyl]phenyl}oxalate, bis{3,4,6-trichloro-2-[(2-ethylbutoxy)carbonyl]phenyl}oxalate, bis{3,4,6-trichloro-2-[(cyclopentylmethoxy)carbonyl]phenyl}oxalate, bis{3,4,6-trichloro-2-[(2-methylhexyloxy)carbonyl]phenyl}oxalate, bis{3,4,6-trichloro-2-[(3-methylhexyloxy)carbonyl]phenyl}oxalate, bis{3,4,6-trichloro-2-[(4-methylhexyloxy)carbonyl]phenyl}oxalate, bis{3,4,6-trichloro-2-[(5-methylhexyloxy)carbonyl]phenyl}oxalate, bis{3,4,6-trichloro-2-[(cyclohexylmethoxy)carbonyl]phenyl}oxalate, bis{3,46-trichloro-2-[(phenylmethoxy)carbonyl]phenyl}oxalate, bis{3,4,6-trichloro-2-[(2-phenylethoxy)carbonyl]phenyl}oxalate, bis(3,4,6-trichloro-2-{[(2-methylphenyl)methoxy]carbonyl}phenyl)oxalate, bis(3,4,6-trichloro-2-{[(3-methylphenyl)methoxy]carbonyl}phenyl)oxalate, bis(3,4,6-trichloro-2-{[(4-methylphenyl)methoxy]carbonyl}phenyl)oxalate, bis(3,4,6-trichloro-2-{[(2,3-dimethylphenyl)methoxy]carbonyl}phenyl)oxalate, bis(3,4,6-trichloro-2-{[(2,4-dimethylphenyl)methoxy]carbonyl}phenyl)oxalate, bis(3,4,6-trichloro-2-{[3,4-dimethylphenyl)methoxy]carbonyl}phenyl)oxalate, bis(3,4,6-trichloro-2-{[(3,5-dimethylphenyl)methoxy]carbonyl}phenyl)oxalate, bis(3,4,6-trichloro-2-{[(2,6-dimethylphenyl)methoxy]carbonyl}phenyl)oxalate, bis(3,4,6-trichloro-2-{[(2-ethylphenyl)methoxy]carbonyl}phenyl)oxalate, bis(3,4,6-trichloro-2-{[(3-ethylphenyl)methoxy]carbonyl}phenyl)oxalate, bis(3,4,6-trichloro-2-{[(4-ethylphenyl)methoxy]carbonyl}phenyl)oxalate, bis(3,4,6-trichloro-2-{[2-(2-methylphenyl)ethoxy]carbonyl}phenyl)oxalate, bis(3,4,6-trichloro-2-{[2-(3-methylphenyl)ethoxy]carbonyl}phenyl)oxalate, bis(3,4,6-trichloro-2-{[2-(4-methylphenyl)ethoxy]carbonyl}phenyl)oxalate, bis{3,4,6-trichloro-2-[(2-phenylpropoxy)carbonyl]phenyl}oxalate, bis{3,4,6-trichloro-2-[(3-phenylpropoxy)carbonyl]phenyl}oxalate, bis{3,4,6-trichloro-2-[1-naphthalenylmethoxy)carbonyl]phenyl}oxalate, bis{3,4,6-trichloro-2-[2-naphthalenylmethoxy)carbonyl]phenyl}oxalate, bis{3,4,6-trichloro-2-[(2,2-diphenylethoxy)carbonyl]phenyl}oxalate, bis{3,4,6-trichloro-2-[(9-fluorenylmethoxy)carbonyl]phenyl}oxalate, and bis{3,4,6-trichloro-2-[(9-anthracenylmethoxy)carbonyl]phenyl}oxalate.

4. The chemiluminescent system of claim 1, wherein the at least one fluorescer is present in an amount ranging from 0.05 to 0.9 percent by weight based on the total weight of the chemiluminescent system.

5. The chemiluminescent system of claim 1, wherein the at least one inorganic salt is selected from the group consisting of: sodium thiosulphate, potassium thiosulphate, cobalt acetate, copper acetate, lead acetate, cupric chloride, ferric chloride, calcium iodide, potassium iodide, silver nitrate, and a combination thereof.

6. The chemiluminescent system of claim 1, wherein the at least one peroxide is selected from the group consisting of: hydrogen peroxide, sodium peroxide, sodium perborate, sodium pyrophosphate peroxide, urea peroxide, histidine peroxide, t-butylhydroperoxide, peroxynehzoic acid, sodium percarbonate, and a combination thereof.

7. The chemiluminescent system of claim 1, wherein the at least one peroxide is present in an amount ranging from 0.25 to 25 percent by weight based on the total weight of the chemiluminescent system.

8. The chemiluminescent system of claim 1, wherein the at least one catalyst is selected from the group consisting of: dimethylbenzylamine, N,N-dimethyl-1-phenylethylamine, N-ethyl-N-methylbenzyl amine, diethylbenzylamine, N-methyl-N-propylbenzylamine, N,N-dibutylbenzylamine, N,N-bis(1-methylethyl)benzenemethanamine, methyl dibenzylamine, ethyl dibenzylamine, n-propyl dibenzylamine, isopropyl dibenzylamine, butyl dibenzylamine, iso-butyl dibenzylamine, N,N-dibenzyl-2-phenylethanamine, hexyl dibenzylamine, tribenzylamine, 4-methyl-N,N-bis[(4-methylphenyl)methyl]benzenemethanamine, 4-methyl-N,N-bis(phenylmethyl)benzenemethanamine, N-methyl-N-phenylbenzenemethanamine, N-ethyl-N-phenylbenzenemethanamine, N,4-dimethyl-N-phenylbenzenemethanamine, N-propyl-N-phenylbenzenemethanamine, N,N-diphenylbenzenemethanamine, N,N-bis(4-methylphenyl)benzenemethanamine, lithium benzoate, sodium benzoate, potassium benzoate, cesium benzoate, lithium salicylate, sodium salicylate, potassium salicylate, cesium salicylate, lithium o-anisate, sodium o-anisate, potassium o-anisate, cesium o-anisate, lithium p-anisate, sodium p-anisate, potassium p-anisate, and/or cesium p-anisate.

9. The chemiluminescent system of claim 1, wherein the at least one catalyst is present in an amount ranging from 5 to 0.0005 percent by weight based on the total weight of the chemiluminescent system.

* * * * *